(12) United States Patent
Niederhauser et al.

(10) Patent No.: US 11,491,305 B2
(45) Date of Patent: Nov. 8, 2022

(54) METHOD FOR PRODUCING A CATHETER COMPRISING A FPCB

(71) Applicant: Berner Fachhochschule, Technik und Informatik, Biel (CH)

(72) Inventors: Thomas Niederhauser, Oberwangen b. Bern (CH); Gerhard Kuert, Magglingen (CH)

(73) Assignee: Berner Fachhochschule, Technik und Informatik, Biel (CH)

( * ) Notice: Subject to any disclaimer, the term of this patent is extended or adjusted under 35 U.S.C. 154(b) by 0 days.

(21) Appl. No.: 17/051,841

(22) PCT Filed: May 2, 2019

(86) PCT No.: PCT/EP2019/061240
§ 371 (c)(1),
(2) Date: Oct. 30, 2020

(87) PCT Pub. No.: WO2019/211376
PCT Pub. Date: Nov. 7, 2019

(65) Prior Publication Data
US 2021/0316113 A1 Oct. 14, 2021

(30) Foreign Application Priority Data
May 2, 2018 (EP) .................................... 18170468

(51) Int. Cl.
*B29C 51/02* (2006.01)
*A61M 25/00* (2006.01)
(Continued)

(52) U.S. Cl.
CPC ....... *A61M 25/0012* (2013.01); *H01R 12/592* (2013.01); *B29C 51/02* (2013.01); *B29C 63/0069* (2013.01)

(58) Field of Classification Search
CPC ......................... A61B 5/6852; A61M 25/0012
See application file for complete search history.

(56) References Cited

U.S. PATENT DOCUMENTS

| 8,147,486 B2 | 4/2012 | Honour et al. |
| 2012/0130218 A1* | 5/2012 | Kauphusman ......... A61B 5/287 600/373 |

(Continued)

FOREIGN PATENT DOCUMENTS

| EP | 1714610 A1 | 10/2006 |
| EP | 3292885 A1 | 3/2018 |

(Continued)

OTHER PUBLICATIONS

Written Opinion of the International Searching Authority for International Application No. PCT/EP2019/061240 (Year: dated 2020).*

(Continued)

*Primary Examiner* — Alison L Hindenlang
*Assistant Examiner* — Debjani Roy
(74) *Attorney, Agent, or Firm* — The Webb Law Firm (57) ABSTRACT

A method for producing a catheter includes inserting a temporary mandrel into a catheter tube, followed by pre-shaping a FPCB in a round hollow cylindrical shape and position it on the catheter tube. Then a shrink tube is positioned around the FPCB on the outside of the catheter tube. The assembly is preheated to the point that the shrink tube has fully contracted and directly contacts and closes the FPCB around the catheter tube. Then the assembly is heated above the melting temperature of the catheter tube to reflow the catheter tube material around the FPCB inside the shrinking tube. After a resting period to allow solidification of the assembly material the mandrel is removed from the inner lumen of the re-solidified catheter tube, and finally the shrink tube is removed.

14 Claims, 10 Drawing Sheets

(51) Int. Cl.
*H01R 12/59* (2011.01)
*B29C 63/00* (2006.01)

(56) References Cited

U.S. PATENT DOCUMENTS

| | | |
|---|---|---|
| 2012/0271135 A1 | 10/2012 | Burke et al. |
| 2014/0378803 A1 | 12/2014 | Geistert et al. |
| 2015/0005799 A1 | 1/2015 | Lindquist et al. |
| 2016/0228061 A1 | 8/2016 | Kallback et al. |
| 2016/0270732 A1 | 9/2016 | Kallback et al. |
| 2017/0068792 A1* | 3/2017 | Reiner .................. A61B 5/0022 |

FOREIGN PATENT DOCUMENTS

| | | |
|---|---|---|
| KR | 1020080078202 A | 8/2008 |
| KR | 1020170003891 A | 1/2017 |
| KR | 101704801 B1 | 2/2017 |
| WO | 2013074036 A1 | 5/2013 |

OTHER PUBLICATIONS

Inoue et al., "Liquid Crystal Polymer Film High Heat Resistance and High Dimensional Stability", Proc. Pan Pacific Microelect. Symp., Feb. 2001, pp. 273-278.
Tae et al., "Liquid Crystal Polymer (LCP)-based Neural Prosthetic Devices", Biomed Eng Lett, 2016, pp. 148-163, vol. 6, No. 3, DOI: 10.1007/s13534-016-0229-z.

* cited by examiner

METHOD FOR PRODUCING A CATHETER COMPRISING A FPCB

CROSS-REFERENCE TO RELATED APPLICATIONS

This application is the United States national phase of International Application No. PCT/EP2019/061240 filed May 2, 2019, and claims priority to European Patent Application No. 18170468.5 filed May 2, 2018, the disclosures of which are hereby incorporated by reference in their entirety.

BACKGROUND OF THE INVENTION

Field of the Invention

The present invention relates to a method for producing a catheter comprising a FPCB as well as a catheter manufactured according to said method,

Description of Related Prior Art

Flexible printed circuit boards (FPCB) have become of tremendous importance for applications where space is restricted and parts of an electronic system are required to have an intrinsic bendability. Thompson D., Kingsley N., Wang G., Papapolymerou J., Tentzeris M. M. et al. have shown in "Liquid crystal polymer film heat resistance and high dimensional stability", Proc. Pan Pacific Microelect. Symp. 2001: 273-278, that liquid crystal polymers (LCP) can be used as dielectricum in applications for FPCB's. Due to its biocompatible nature and water impermeability, it is well suited for the application in medical devices such as neuroprosthetic implants as mentioned by Tae M. G., Chaebin K., Soowon S., Jeong H. P., Jin H. K., Sung J. K. et al. or cardiovascular catheters in "Liquid crystal polymer (LCP)-based neural prosthetic devices" in Biomed Eng Letters. 2016, Volume 6, Issue 3, pp 148-163. For the latter, the state of the art manufacturing process is labor intense and expensive. The use of process automation is limited due to the small size and fragility of the single components, which in turn inhibits an automated large scale production.

Current technologies for attaching a FPCB on a catheter rely on bonding, ultrasonic welding or other mechanical means are known from US 2014/378803 A1 "Catheter and method for producing the same" for W. Geistert as well as from US 2016/228061 A1 "Low profile medical device with integrated flexible circuit and methods of making the same" for B. Kallback and U.S. Pat. No. 8,147,486, "Medical device with flexible printed circuit" for K. Honour et al.

These processes usually result in catheters with a high stiffness because the edges have been glued or welded together in order to establish a tubular structure. Such catheters are limited to specific applications where no bendability is required.

The majority of the bonding processes are promoting additives as key element to adhere the FPCB, which are generally sensitive to environmental conditions and additive dosage. Furthermore, the presence of adhesives is undesirable in a cleanroom setting.

US 2015/005799 A1 "Renal nerve modulation ballon having improved robustness" for J. S. Linguist et al. uses a laser etching onto the surface of the catheter to reach improved adhesion properties while bonding.

US 2012/0271135 "Flexible electrode assembly for insertion into body lumen or organ" for J. A. Burke et al. discloses the insertion of a FPCB in a single or multi lumen tube and it's expansion on the distal end of the catheter. The presented catheter is configured to be used as an esophageal diagnostic device for the detection of paroxysmal arrhythmias.

WO 2013/074036 discloses a catheter component made from a single piece of flexible material having at least one layer of an electrically conductive line or layer on its surface, comprising an elongated, flexible middle section with circular cross-sectional area formed from rolling and fastening tighter a central portion of said flexible material; and two substantially flat end portions.

US 2016/270732 discloses a thin walled elongated hollow lumen catheter where a flexible circuit comprises the entire inner lumen and the outer lumen is comprised of a polymer extrusion. The cylindrical flexible circuit is configured in such a way to carry at least part of the device structural loads and therefore reduce the medical device total wall thickness.

SUMMARY OF THE INVENTION

Based on this prior art, it is an object of the present invention to provide an improved method to produce a bendable medical device, especially a catheter, comprising passive and active electronic components.

This object is achieved with a lamination process as method for producing a catheter by inserting a temporary mandrel into a catheter tube, followed by preshaping a FPCB in a round hollow cylindrical shape and positioning it on the catheter tube. Then a shrink tube is positioned around the FPCB on the outside of the catheter tube. The assembly is preheated to the point that the shrink tube has fully contracted and directly contacts and closes the FPCB around the catheter tube. Then the assembly is heated above the melting temperature of the catheter tube to reflow the catheter tube material around the FPCB inside the shrinking tube. After a resting period to allow solidification of the assembly material the mandrel is removed from the inner lumen of the re-solidified catheter tube, and finally the shrink tube is removed.

The method for producing a catheter uses a FPCB having at least one electrode segment at its distal end portion and a FPCB tail leading to a connector at its proximal portion. Various numbers of electrode segments are possible. The FPCB can also comprise delamination preventing holes, preferably at the edges around the electrode segments as well as on the FPCB tail. The preferred method comprises several steps, wherein some of them are optional: a mandrel inserting step, wherein a temporary mandrel is inserted into a catheter tube, a FPCB preshaping step, wherein the electrode segment of the FPCB is preshaped in a round hollow cylindrical shape, a FPCB positioning step, wherein the preshaped FPCB is positioned on the catheter tube, a shrink tube positioning step, wherein a shrink tube is positioned around the assembly comprising the FPCB and the catheter tube on the outside, a shrink tube contracting step wherein the assembly including the shrink tube is preheated to the point that the shrink tube has fully contracted and directly contacts and closes the FPCB around the catheter tube, a reflow step, wherein the assembly is heated above the melting temperature of the catheter tube to allow the catheter tube material to flow around the FPCB inside the shrink tube, a cooling step, wherein the assembly rests until solidification of the assembly material, a mandrel removing step, wherein the mandrel is removed from the inner lumen of the re-solidified catheter tube, and a shrink tube removal step, wherein the shrink tube is removed. This method allows a delamination safe embedding of the FPCB on and within the catheter tube.

It is possible to add further reflow material, e.g. a sheet of catheter tube like material, around the FPCB, wherein the reflow material has a melting temperature similar to the melting temperature of the catheter tube material. This reflow material can comprises more than one layer as 1½ to two layers of a thin sheet to provide already a cover sheet on the FPCB. The aim is to ensure that the FPCB is well encased between the mandrel and the shrink tube to allow the catheter and any additional material to flow around any embedded FPCB structure, especially also delamination preventing holes. They can be provided near the edges of the electrodes and/or on a connecting segment of the FPCB tail. In the reflow step, the heating is conducted in a way allowing the catheter tube material to flow through and around the delamination preventing holes.

A placement monitoring step can be provided after the shrink tube contracting step to check the positioning of the shrink tube. If the position is estimated non sufficient, the shrink tube positioning step is then repeated.

A reflow checking step can be provided after the reflow step to check if the catheter tube material has fully reflowed the surrounding FPCB and inside the shrinking tube.

The shrink tube removal step can comprise providing a cut in each side of the shrink tube and peeling it off the laminated unit of FPCB and catheter tube material.

The FPCB positioning step can also comprise cutting an FPCB tail passage hole in the catheter tube and feeding through the FPCB tail inside the catheter tube so that only the electrode part is provided on and below the reflowed coating of the catheter tube.

A guide wire can then be connected with the connector, preferably through one or more holes in the connector.

Before the shrink tube contracting step, a hole covering step can be provided, within which the hole is covered by a cut out, Within the FPCB positioning step, the preshaped FPCB can be held directly or indirectly via the clamping of the temporary mandrel.

The FPCB comprises a plurality of delamination preventing holes provided near the edges of the electrodes and/or on a connecting segment of the FPCB tail, wherein, in the reflow step, the heating is conducted to allow the catheter tube material to flow through the delamination preventing holes. Before the shrink tube positioning step, a material adding step can be provided, wherein a sheet of reflow material is provided around the FPCB. Said reflow material has a melting temperature similar to the melting temperature of the catheter tube material and provides an additional material coating on the FPCB below the shrinking tube.

The preshaped FPCB has preferably a predetermined width being smaller compared to the circumference of the catheter tube so that, within the FPCB positioning step, when the FPCB is positioned on the catheter tube on the circumference, the opposite electrode edges, being parallel in the longitudinal direction of the catheter, do not touch or overlap. Between them is preferably a small gap.

Within the reflow step, the assembly is heated above the melting temperature of the catheter tube with hot air or thermal radiation directed towards the catheter assembly. It is only necessary to observe that the heating is sufficient to heat the assembly to a temperature higher than the melting temperature of the catheter material but lesser than the melting temperature of the shrinking tube and the melting temperature of the mandrel and the melting temperature of the FPCB base material. Since the FPCB is LCP, this is usually observed.

The method can also comprise a reflow step to adhere a FPCB to a TPU tubular body using a laser welding process in combination with a delamination preventing hole structure in the FPCB. The laser welding process does not weld LCP on LCP, it does weld TPU to LCP. The welding seam is preferredly placed just on the edge of LCP material connecting LCP to TPU.

Figure 3:
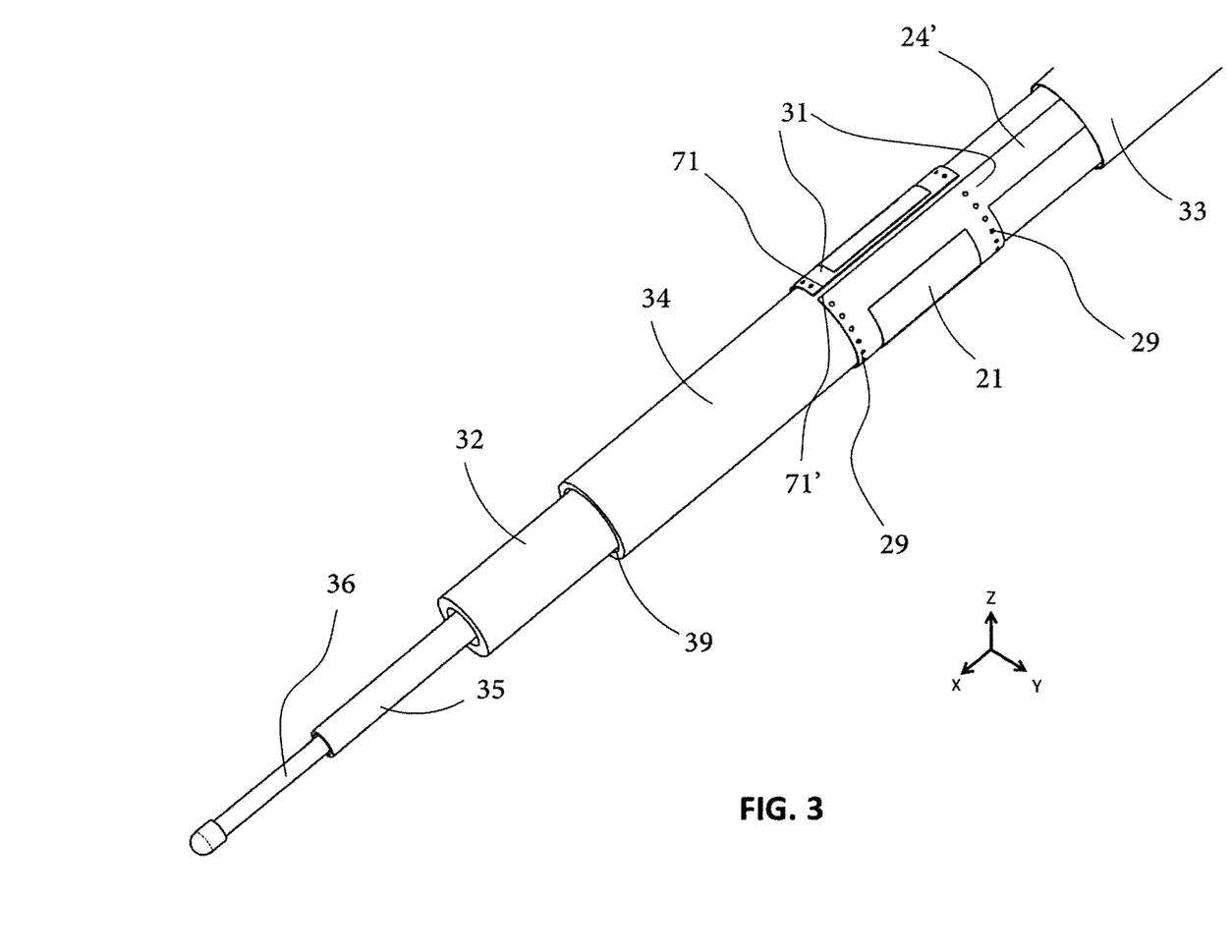
FIG. 3 shows a schematic view of a lamination assembly according to an embodiment of the invention.
Figure 5:
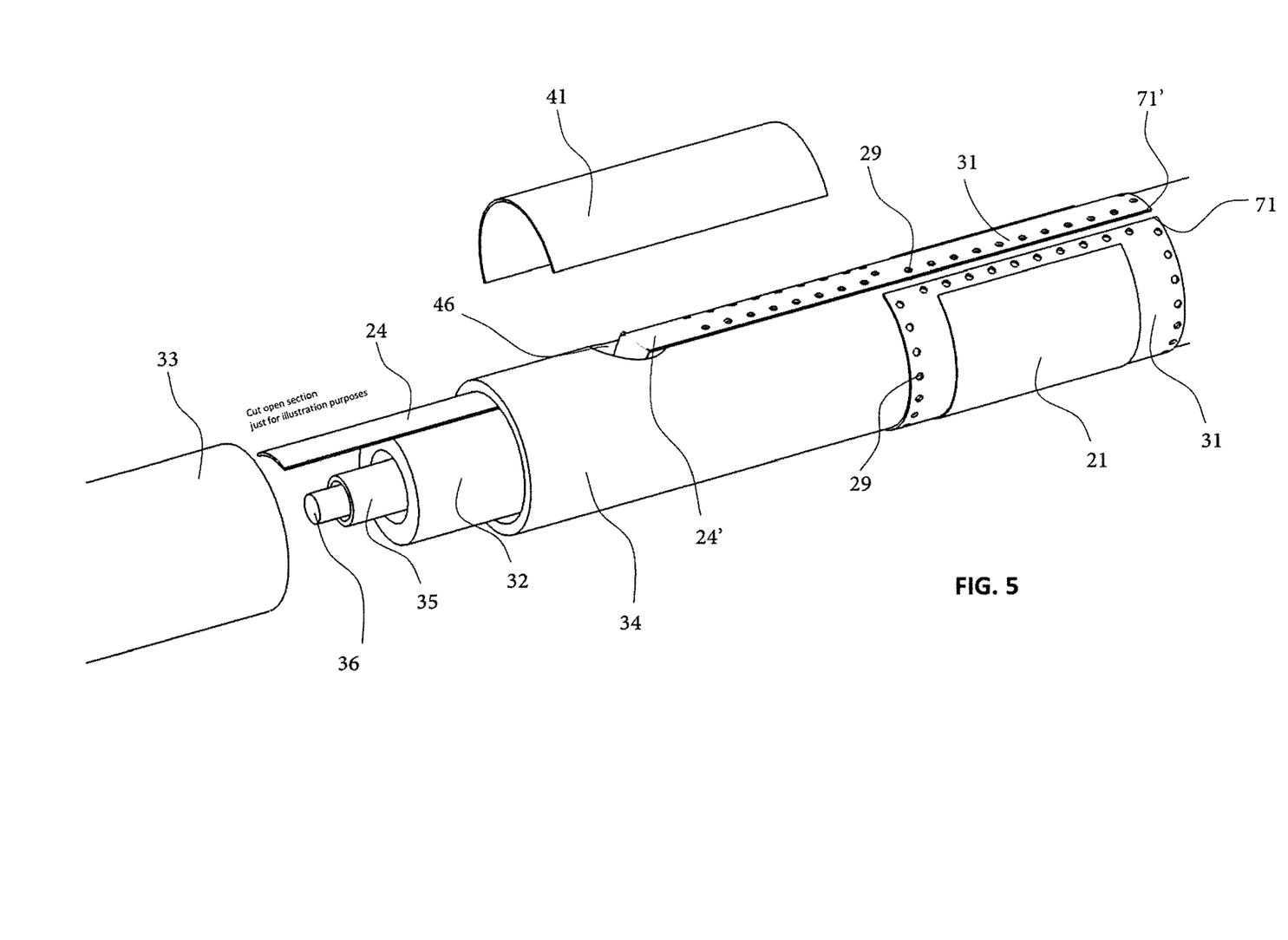
FIG. 5 shows a perspective exploded view of a lamination process according to an embodiment of the invention.

It is possible to have different materials as TPU for the catheter tube and apply a different alternative heating. Then, within the reflow step, laser radiation is directed to the edges of the FPCB and/or FPCB tail to weld the LCP material edge of the FPCB material to the catheter tube. As mentioned above, preferredly the catheter tube is made of TPU. Here, it is only important that this catheter material is a laser opaque material, whereas the shrinking tube materials are usually laser transparent materials. The welding can take place by directing the laser on a specific spot, where the waist of the laser beam is located at a space between the mandrel surface and the inner shrinked shrinking tube surface. Then it is possible to rotate the catheter assembly to weld around the circumference, e.g. the longer side edges of electrodes as shown in FIGS. 3 and 5, and to displace the catheter assembly in the longitudinal direction of the catheter to weld the opposing edges of the electrodes which are oriented in parallel with the gap in between in the longitudinal direction of the catheter.

After the reflow step provided as a laser welding step, it is possible to add a smoothing heating step, wherein the assembly is heated above the melting temperature of the catheter tube with hot air or thermal radiation directed towards the catheter assembly to additionally laminate the catheter with the FPCB material. This allows avoiding protrusions stemming from welding seams.

A catheter comprising at least one electrode segment at its proximal end portion and a FPCB tail leading to a connector at its distal portion, wherein the circumferential width of the FPCB is chosen providing a gap between the edges of the FPCB, can be manufactured according to the method comprising a combination of the features as mentioned above.

A catheter comprising at least one electrode segment at its proximal end portion and a FPCB tail leading to a connector at its distal portion, wherein the FPCB comprises a plurality of delamination preventing holes provided near the edges of the electrodes and/or on a connecting segment of the FPCB tail, can be manufactured according to the method comprising a combination of the features as mentioned above.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Figure 1:
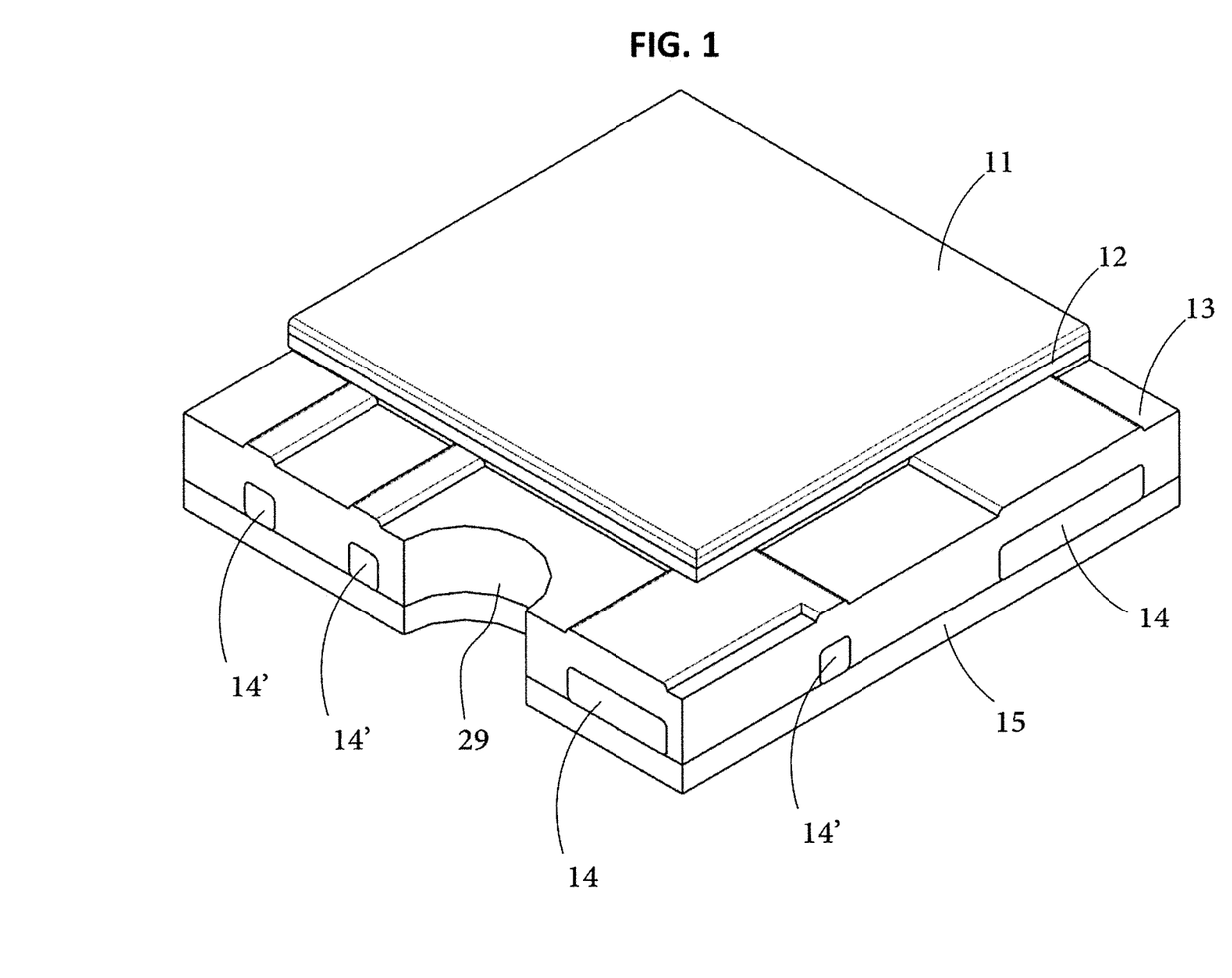
FIG. 1 shows the stack layout of an embodiment of the flexible printed circuit board part of a catheter according to an embodiment of the invention.

FIG. 1 shows the stack layout of an embodiment of the flexible printed circuit board part of a catheter according to an embodiment of the invention. A flexible printed circuit board (FPCB) which is adhered to the catheter tube 31 for the medical product to be produced, has a single signal layer (comprising a plurality of elements 14 and 14') with a dielectricum 13 based on liquid crystal polymer (LCP) and the stack layout given as shown in FIG. 1. On a cover layer 15, made from LCP Ultralam 3809, a commercially available product from Rogers Corporation, Chandler, Ariz., USA, there is provided a base copper or gold layer with structured traces 14, 14' of different width within a flex layer 13 made from LCP Ultralam 3850 HT, a further LCP product from Rogers. The base layer provides the conducting circuit board elements 14 and 14' as well embedded in the flex layer 13. The flex layer 13 covers all conducting circuit board elements 14 and 14' so that they are completely embedded in the flex layer 13. The upper side of the flex layer, i.e. on the opposite side of the cover layer 15, is provided a plated copper sheet 12 covered by a surface finish 11 of ENIG-AU-Ni according to the standard IPC-4552 comprising a specification for electroless nickel/immersion gold plating for printed circuit boards. However, ENIG is non-biocompatible and other biocompatible choices for the surface finish can be gold, platinum, or platin-iridium as surface finish.

Figure 2A:
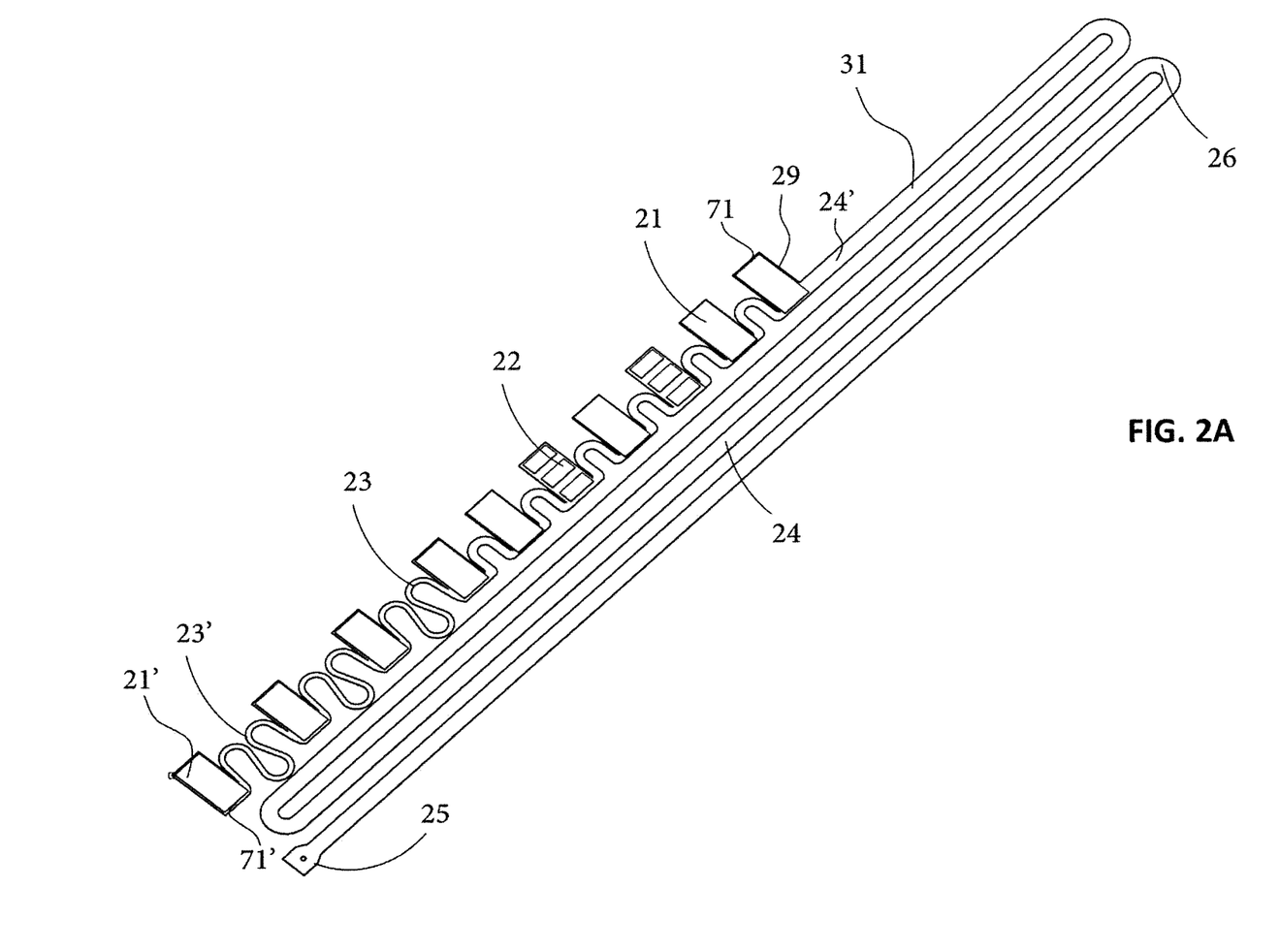
FIG. 2A shows a flexible printed board in a planar form before integration within a medical device as a catheter.
Figure 2B:
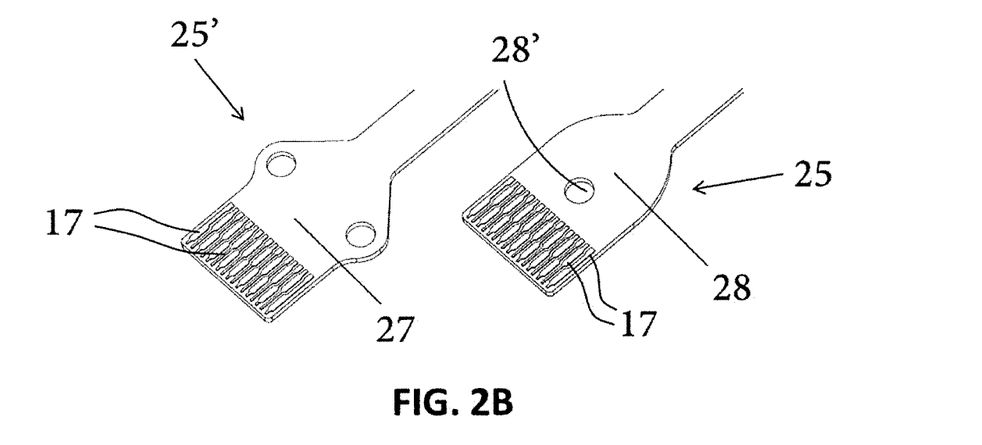
FIG. 2B shows, in a detail view, two alternative ZIF connectors for the free proximal end of the flexible printed board of FIG. 2A.

All conducting circuit board elements 14 and 14' are all gold/copper traces with different widths, running through the FPCB and connecting electrodes 21' through one or more meanders 23' all the way to the connector 25, where they are connected to one specific contact 17 as shown in FIG. 2B within connector 25.

The electrodes shapes (length, widths, numbers) and the distances shown are examples can be arbitrary and are not limited with the FPCB. The same applies to wall thickness of different elements.

FIG. 2A shows a flexible printed board in a planar form before integration within a medical device as a catheter. The design shown in FIG. 2A has fourteen electrodes, here of two types 21 and 22, arranged in a distance of 10 millimetres up to 15 millimetres one from another. Within these electrodes, there are plates which will become ring electrodes 21 and split electrodes 22, here with three adjacent electrodes. The three electrodes of one split electrode 22 are arranged one beside the other in a direction perpendicular to the direction of electrodes 21 and 22, so that the single electrodes are arranged in the ring of a catheter around the circumference. Between each electrode 21, 22 in the longitudinal direction there is a flexible element 23, which follows a meander shaped pattern, usually designated as Ω shape (omega shape). This pattern can also be described as an "M" or "W". Further embodiments of the electrode connections can follow the stretchable electrode conductor assembly as dislcosed in EP 3 292 885 A1. The attachment of the flexible element 23 is preferably attached at a corner of the electrode 21 and 22, here near edge 71' of the electrode 21. The width of these meanders of the flexible element 23 get progressively smaller proportional to the number of traces in order render the catheter more flexible towards its distal end. Smaller means flatter and/or less width. In other words, each meander starting from the most proximal electrode 21 in the distal part has and comprises less electrical lines to contact the next following electrodes 21, 22 until the most distal electrode 21', where the last meander 23' only comprises the traces necessary to contact the electrode elements of this most distal electrode 21'. Various different designs are possible for these electrode-electrode connections 23 including an alternating and straight spiral. The aim is to improve the bending characteristics during e.g. nasal or oral insertion.

The different segments of the FPCB tail 24, i.e. the connection between the distal end and the proximal end with the single hole connector 25 can be manufactured with bended segments 26 in a 180 degree manner as shown in FIG. 2A in a planar way. The bends are later folded to form a straight line which can have a total length of e.g. 800 mm. A similar approach is shown in EP 1 714 610 B 1. It is noted that the electrode 21 or 22 in FIG. 2A comprises the actual electrode surface as shown in FIG. 2C and FIG. 3 and surrounding FPCB portions, optionally comprising a sequence of adjacent surrounding holes 29 as indicated in FIG. 2C and FIG. 3.

FIG. 2B shows, in a detail view, two alternative ZIF connectors 25 and 25' for the free proximal end of the flexible printed board of FIG. 2A. On the proximal end of the catheter tube a MOLEX 17 pole zero insertion force (ZIF) connector, provided by Molex LLC, USA, with a pitch of 250 micrometer is placed. Out of the seventeen pads the three inner most pads 17 have been left unconnected allowing the ZIF connector 25, 25' to be fully foldable in the center section. The ZIF connector 25, 25' has to be supported by a polyamid plate 27 or 28 with a thickness of 100 micrometer in order to fit in the female ZIF connector (not shown). The one or two holes 28' in the connectors are used to bind an insertion wire, which is pulled through the catheter together with a laser etched PTFE liner used to hold a guide wire.

Figure 2C:
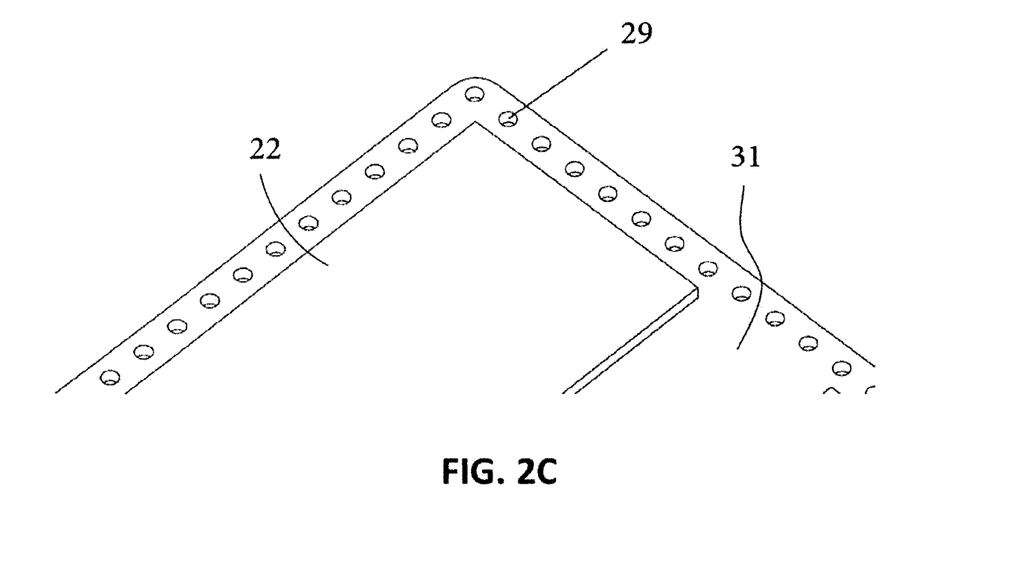
FIG. 2C shows, in a detail view, the edges of an electrode of the flexible printed board of FIG. 2A.

FIG. 2C shows, in a detail view, the edges of an electrode of the flexible printed board of FIG. 2A. To prevent the onset of FPCB edge delamination and to increase the peel strength there is a series of holes 29 placed on the edge of the FPCB, i.e. around the electrodes 21. The holes 29 are intended to fill with the catheter tube material during lamination. The average diameter of holes 29 is 120 micrometer with 300 micrometer interhole distance. The holes 29 were laser cut during manufacturing of the LCP and they cover the contour for a segment with the length of 120 mm. PUR 85 Pellethane® 2363 80A extrusion is used as material for the catheter tube. PU, TPU, Silicome or similar materials can be used as well. The main property of the catheter and additional material is a lower melting temperature in comparison to the melting temperature of the shrink tube and the melting temperature of the inner mandrel.

As mentioned above, in the FPCB 31 are provided delamination preventing holes 29 that fill with the material of the catheter tube 34 during the lamination process or through addition of further material connecting with the catheter tube material. These holes 29 can be laser cut, punched, melted, cut, milled or brought into the FPCB 31 by any other means. They can be an intrinsic part of the layer stack during the creation of the FPCB 31. The delamination preventing holes 29 can have any dimension, shape and depth. They can be connected by a grid of indentations or can be blind or buried within the FPCB 31. They can be placed on any location on the FPCB 31 with any orientation, although providing them near the edges 71, 71' of the electrodes or along the connecting segment 24', also in a single line there (not shown in the drawings, which show a double line).

FIG. 3 shows a schematic view of a lamination assembly according to an embodiment of the invention comprising the FPCB 31, a PTFE mandrel 32, PTFE shrinktube 33, a catheter tube 34 and a guidewire 36 held by a PTFE tube 35.

The guide wire 36 is surrounded by the PTFE tube 35. This PTFE tube 35 is inside the hollow PTFE mandrel 32 which is inside the hollow sleeve of the catheter tube 34, onto which the flexible printed circuit board 31 is positioned. Finally this combination of catheter tube 34 and flexible printed circuit board 31 is surrounded by a PTFE shrink tube 33. The elements 32, 33 and 35 are made in PTFE. It is also possible to replace the material of the PTFE mandrel 32 by a PTFE or ePTFE coated stainless steel mandrel or glass fibre reinforced PTFE.

The FPCB 31 comprises, as shown in FIG. 2A the electrodes 21. All four edges (comprising the opposite edges 71 and 71') of the electrode portion of the flexible printed circuit board 31 have the sequence of holes 29 as shown in FIG. 2C. The width of the flexible printed circuit board 31 with the electrode 21 is such that the edges 71 and 71' are almost tin contact at the circumference of catheter tube 34. It is noted that the holes 29 can also be provided on the FPC across the attachment of the trace 31 or meander 23. The holes 29 are here, as alternative to FIG. 2C where the holes entirely surround the electrode supporting FPCB element 21, only provided along the longer edge portion of the electrode portion and not along the opposite edges 71 and 71'. The extruded catheter tube 34 in an example has an outer diameter of 3 mm and a wall thickness of about 250 micrometres. It is possible but of course not mandatory to include a radiopaque stripe with 30% BaSO4 compound (not shown in the drawing). The FPCB tail 24 is positioned under the PTFE shrinktube 33, wherein a connecting segment 24' of the tail 24 is connected to the first and most proximal electrode in the distal part of the FPCB 31. The electrodes are provided in the distal portion of the catheter, the proximal portion is related to the tail 24 with the connector 25.

The FPCB 31 is then laminated through application of heat and pressure. The heat is generated with a commercially available heat gun and pressure is applied with the help of a peelable shrinktube (FluoroPEELZ made by ZEUS), which has a shrink ratio of 1.4 and an inner diameter of 3.32 mm. The catheter lumen 39 is at the same time supported by the PTFE mandrel 32 with an inner diameter of 1.45 mm and a wall thickness of 300 micrometres.

Figure 4A:
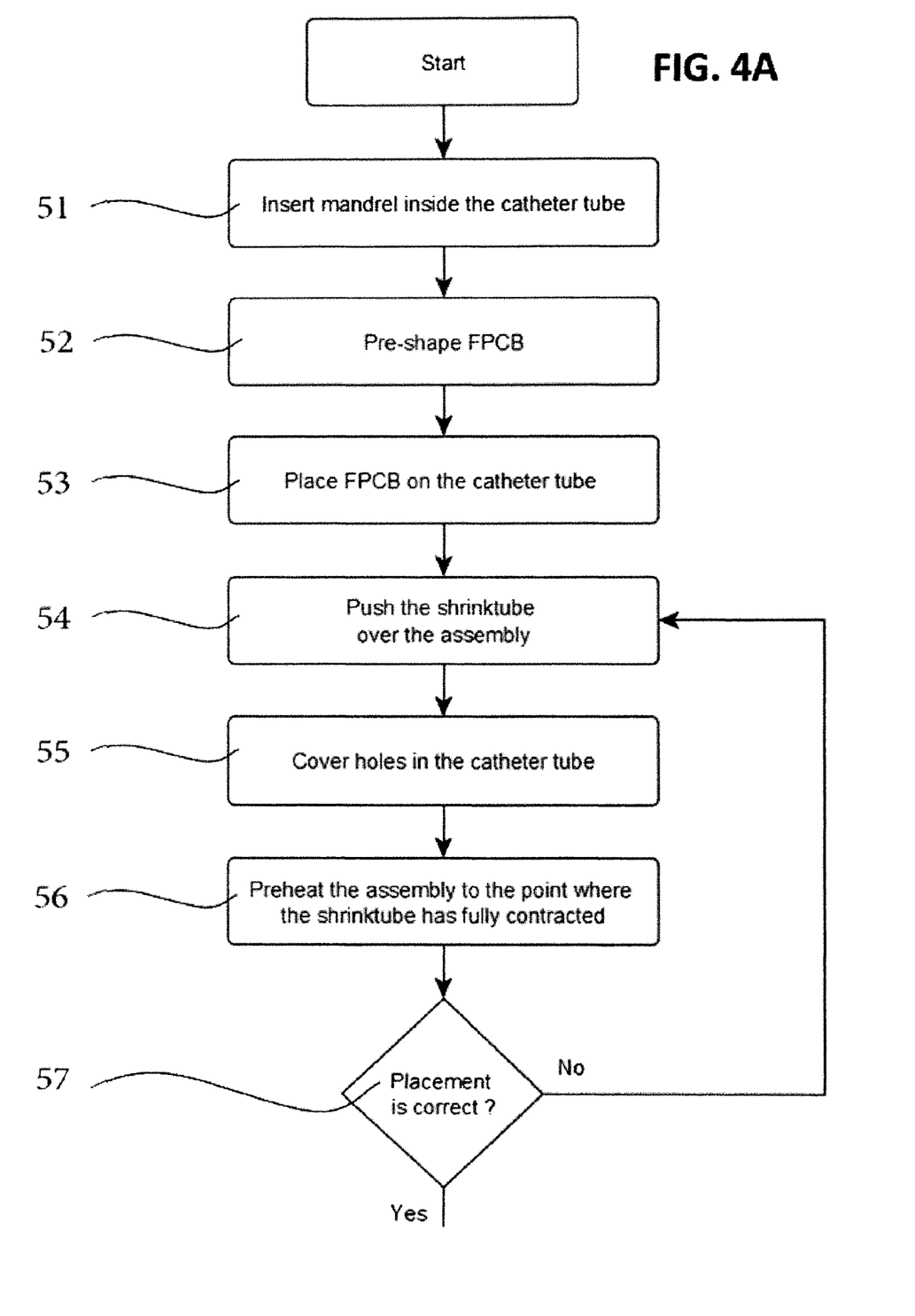
FIGS. 4A & 4B show the lamination process according to an embodiment of the invention.
Figure 4B:
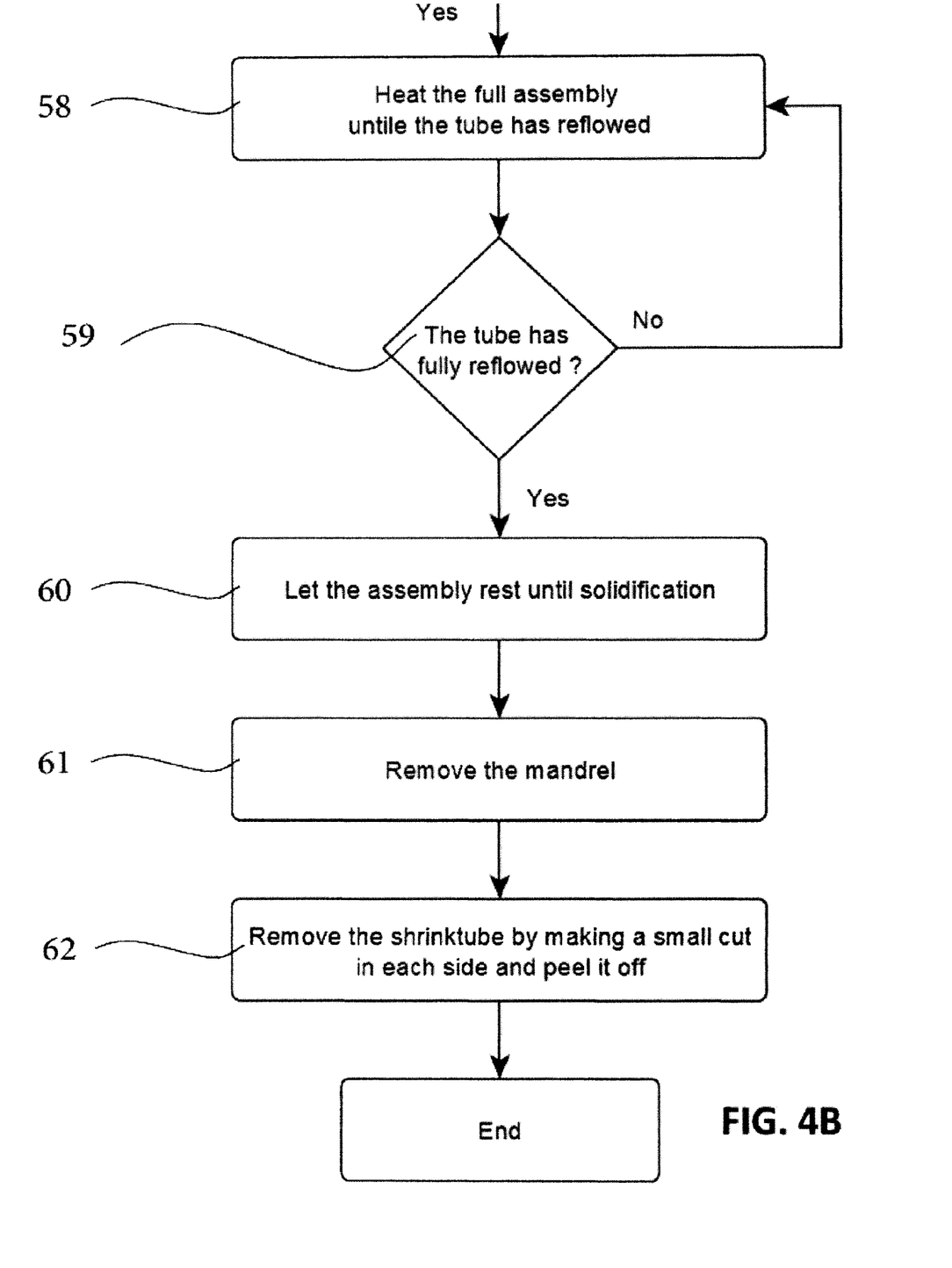

The whole lamination process is subdivided into the phases as illustrated in FIG. 4A and FIG. 4B. FIG. 4A and FIG. 4B are to be read together, since the last step in FIG. 4A continues with the first step of FIG. 4B. FIGS. 4A and 4B show the lamination process according to an embodiment of the invention.

Initially, within a mandrel inserting step 51 a temporary mandrel 32 is inserted into a catheter tube 34. Then the initially flat FPCB 31 is preshaped in a round hollow cylindrical shape in a FPCB preshaping step 52. The preshaped FPCB is positioned on the catheter tube 34, held in place by ductile forces generated as result of the preshaping/bending process during the placing step 53. It is holding on to the catheter tube 34 on its own. The catheter tube 34 is preferably held directly and indirectly via a clamped temporary mandrel 32, in a FPCB positioning step 53. In a shrink tube positioning step 54 the shrink tube 33 is positioned around the assembly with the FPCB 31 on the outside of the assembly. In a hole covering step 55 the hole 46 is covered by a cutout piece 41. In a shrink tube contracting step 56 the assembly as prepared up to this point is preheated to the point that the shrink tube 33 has fully contracted and directly contacts and closes the FPCB 31 around the catheter tube 34 without adhering the different elements. Optionally, the placement of the shrink tube is monitored in a placement monitoring step 57, which includes a decision to restart the shrink tube positioning 54, if the positioning of the shrink tube 33 is not considered of sufficient quality. The monitoring can comprise one or more of the following spatial relationships: The distance in x axis direction from electrode 21 to electrode. (Spacing). The angular alignment of the electrodes 21 rotation around the x axis. The edges 71, 71' of the FPCB 31 should not overlap. Finally, hole cover 41 is placed correctly If the placement monitoring strep 57 is passed, then the full assembly is heated in a reflow step 58 to adhere the different elements together. In an optional reflow checking step 59 it is checked if the catheter tube 34 material has fully reflowed the surrounding FPCB 31 and inside the shrinking tube 33. The TPU melts around the FPCB 31 inside the shrinktube 33. In a cooling step 60 the assembly rests until solidification of these lamination steps. In a mandrel removing step 61 the mandrel 32 is removed from the inner lumen 39. Finally, in a shrink tube removal step 62 the shrink tube 33 is removed. This happens in a preferred lay out by making a small cut in the shrink tube 33 and peeling it off the laminated unit of FPCB 31 and catheter tube 34.

The process is based inter alia on the insight that the catheter tube 34 material has to have a lower melting point than the FPCB. The melting temperature of the catheter tube 34 should be preferably in the range between 150 C and 250 C. The FPCB 31 has to be made out of a material with a melting point above 280 C. The electrode 21, 22 base material, i.e., Cu has a high ductility and malleability, thus, can be easily shaped into a cylindrical form. The inconvenience of Cu is the lack of biocompatibility and therefore gold is a preferred base material.

The method comprises two options for the positioning of the FPCB tail 24. One possibility is on the outside of the catheter tube 34. Then the FPCB tail 24 will be reflowed with the catheter tube material over its entire length and no specific preparation is needed to obtain the connector at the proximal end of the catheter. The second possibility as shown specifically in connection with FIG. 5 is to run the FPCB tail 24 inside the catheter tube 24 so that it is laminated or connected to the inside of the catheter tube 24 which is the preferred setup. Therefore it is necessary to provide the catheter tube 34 with the cut out 46 at the beginning. Then, an insertion rod is provided having a pulling wire connection at its front end. This rod is pushed in the catheter tube 34 until the cut out 46, where the wire is exited from the tube 34 allowing to connect the pulling wire at the connector plate hole(s) 28' of the connector 25 of the FPCB 31. When this insertion rod is now pushed to the proximal end of the catheter the FPCB tail 24 is taken with it and feeded through the cut out 46 just under the catheter tube 34 above the insertion rod. Then the insertion rod is removed and the FPCB tail 24 has already the position as shown in FIG. 5.

Then a PTFE mandrel 32 is inserted in the single lumen catheter tube 34, whereby the outer diameter of the PTFE mandrel 32 matches the inner diameter of the catheter tube 34 with the proviso allowing the place for the already positioned FPCB tail 24. The components are assembled as illustrated in FIG. 3 or FIG. 5, i.e. inside the mandrel 32 are provided the PTFE tube 35 with the inner guide wire 36 preferredly inside the catheter tube 34. The connector 25 as end of the FPCB tail 24 is inside the catheter tube 34 and the connecting segment 24' is positioned outside on the catheter tube 34. This is achieved by leading the FPCB tail 24 with the guide wire 36 through said hole 46 in the catheter tube 34.

The shrink tube 33 is preheated to provide the full effect of the shrinking tube 33. The amount of heat applied is sufficient for a shrinking effect of the shrink tube 33 but the temperature is not so high that the full shrinking takes place of that the catheter tube would become liquid. Then, if the positioning of all elements is correct, a second heating cycle is applied in which the melting temperature of the catheter tube 34 is exceeded. Once the catheter tube 34 material has fully reflown, e.g. for about 60 seconds, a subsequent resting period 60' of about 120 seconds has passed. This resting period 60' is similar as the step 60 in FIG. 4B. The assembly has to cool down and solidify during the resting period. The solidification and resting phase can e.g. be accelerated with the help of pressurized air.

The temporary mandrel 32 is removed through application of the following procedure. First, the entire shrinktube 33 is clamped into a vice, which has a prism to hold cylindrical objects. Then a subsequent (third) reheating cycle to 100 Celsius is applied. The PTFE mandrel 32 inside the catheter tube 34 is removed by a moderate to strong pull. This can happen while being elongated or not. The PTFE mandrel 32 is pulled out of the clamped catheter tube 34. The catheter tube 34 remains static, the PTFE mandrel 32 gets pulled. Afterwards, the FPCB 31 is adhered to a length of 120 mm, and the PTFE shrinktube 33 is removed by making two horizontal cuts in its circumference. The remaining stripes are peeled off by hand. In order to seal the catheter device, the hole through which the FPCB 31 was inserted, is closed during the lamination process with the method illustrated in connection with FIG. 5.

FIG. 5 shows an illustration of the method to provide the hole closure of the catheter according to hole closure step 55. A rectangular piece of TPU, i.e. the cut out piece 41 is placed between the hole 46 and shrink tube 33. The intention is to seal the hole 46 during the lamination process when the cutout piece 41 has reflowed with the catheter tube 34 material. After the lamination process has concluded the catheter has to be tipped with a heatable form, i.e. melting the tip of the catheter tube into a pointed elongated shape.

The elementor cut-out piece 41 to close the hole 46 can be of the same material than the catheter tube 34 or of other origin. The dimensions can include covering the whole circumference of the catheter tube 34 and the hole 46 or just partially covering the catheter tube. A plurality of other cut out 41 shapes can be applied to close holes, adhere components or other means. The hole 46 can also be left uncovered.

The connecting segment 24' of the FPCB tail 24 traverses the catheter tube 34 in the cut out 46. The connecting segment 24' as shown in FIG. 5 comprises a double line of holes 29 to be attached in this segment on the existing catheter tube 34.

Beside the lamination in conjunction with the use of the delamination preventing holes 29 creating a microhole structure, it is possible to use a laser welding process to attach the FPCB 31 to the catheter tube 43.

Figure 6:
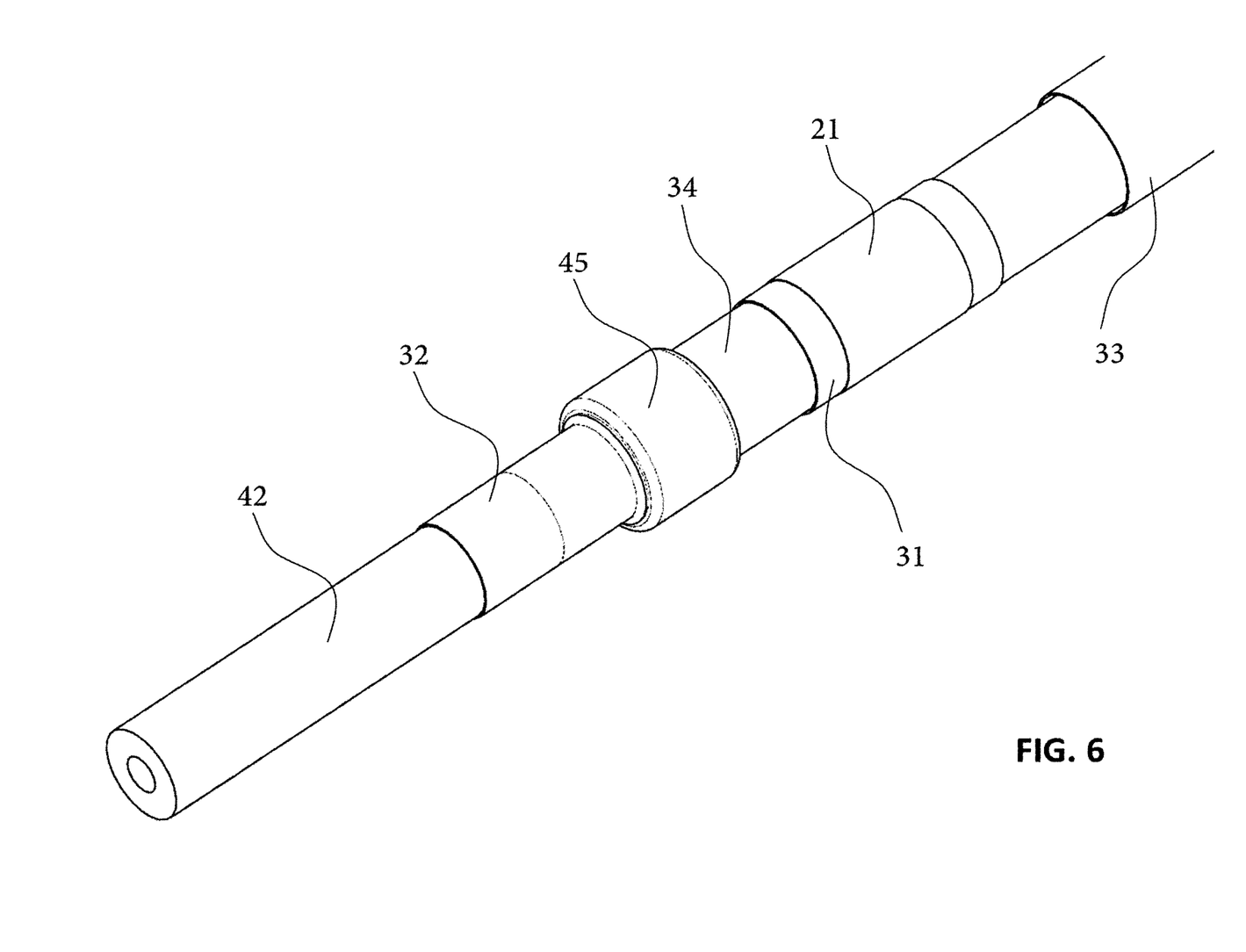
FIG. 6 shows a perspective exploded view of a laser welding process according to an embodiment of the invention.

Within a test setup for a laser welding process, the process was monitored with a 3 axis CO2 laser (Model BWTec type 1410) having a wavelength between 10570 and 10630 nm. A stainless steel mandrel 42 is inserted inside a PTFE mandrel 32, which is placed in the lumen 39 of the catheter tube 34, whereby the end of the catheter tube 34 is held in place by an adhesive tape 45 as shown in FIG. 6, i.e. wound around at the end portion of the PTFE mandrel 32. The steel mandrel 42 can then be clamped at the end extending beyond the PTFE mandrel 32 and the adhesive tape 45 in the chuck of the laser machine. The initially flat FPCB 31 is rounded with the radius of 1.5 mm and placed on the catheter tube 34. The shrink tube 33 with an inner diameter of 3.32 mm is moved over the assembly and then heated by the laser using a 360 perpetual turning motion around the longitudinal axis of the steel mandrel 42. After this process step, the edges 71 and 71' of the FPCB 31 are welded on to the polyurethane tubular body of the catheter tube 34, placing the laser welding seam on a space with the width of 1.3 mm. Different laser parameters can be used for axial and rotary motions, e.g. an advance of the laser along the longitudinal axis for 20 to 70 mm/minute. The shrink tube 33 preparation can be done with a turning rate of 200 turns/minute and an advance feed rate of 150 mm/minute.

After the full contour of the FPCB 31 is laser welded, the stainless steel mandrel 42 and the shrinktube 33 are removed from the catheter tube 34. To smoothen the surface of the catheter an additional reflow process step is applied. This specific reflow process, i.e. a heating process, starts at step 54 of the flowchart in FIG. 4B after removal of the laser cut leaving the laser cut hole 46.

For both lamination and laser welding, there is no danger of harming electrical conductivity. The probability of a connector tearing off during insertion into a catheter tube has to be rated higher than damaging a trace through lamination. The introduction of the catheter trough the nasal cavity should not pose any challenges since the tests with the nasal insertion test gauge were successful. Although some kinking of the catheter can occur between the electrodes 21, 22, this does not generate enough shearing strength to damage the FPCB 31 or the TPU tube 41 as part of the catheter tube 34. If the laser power is unstable, the laser welding process can be applied multiple times at the same location, which results in a "smearing" of larger laser power variations. Another drawback of the laser welding is associated with the protrusions on the surface of the welding seam. In order to reach the required surface smoothness the laser welded catheters should be subsequently laminated. i.e. the reflow step of the lamination process should be applied as subsequent step. The advantage of this 2-step approach in view of connecting the FPCB 31 with the catheter tube 34 is that the welding allows a specific well defined heat application at the specific predetermined place. The general heating of the assembly by hot air or thermal radiation is less oriented but can smoothen possible protrusions as created by the initial welding step.

Figure 7A:
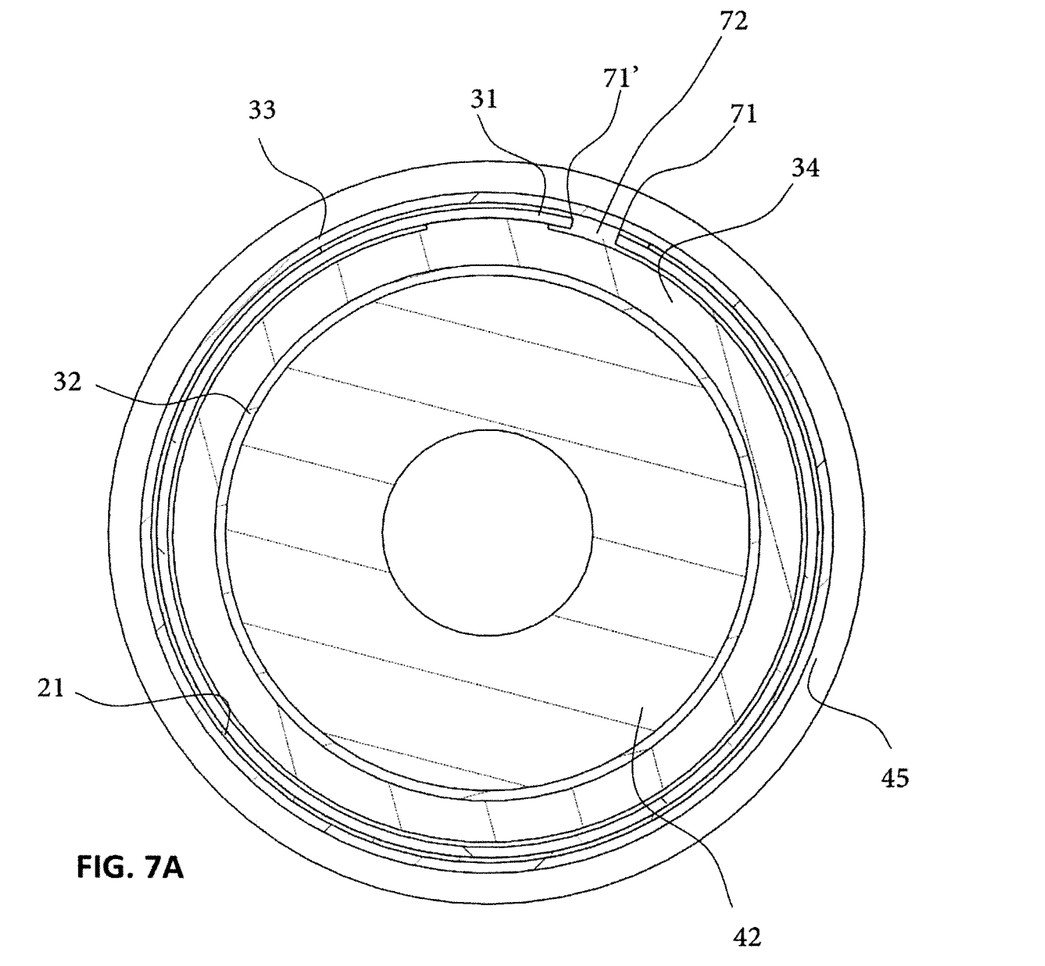
FIG. 7A shows a cross-section view of the lamination assembly of FIG. 6 in the distal segment.

FIG. 7A shows a cross-section view of the lamination assembly of FIG. 6 in the proximal electrode segment. The assembly is covered by the adhesive tape 45 adjacent to the shrink tube 33. Inside is the steel mandrel 42 covered by a temporary PTFE mandrel, positioned inside the catheter tube 34. On the catheter tube is provided the FPCB 31 including the ring electrode 21, wherein the edges 71 and 71' of the FPCB 31 do not overlap but allow for a small gap 72.

The circumferential width of the FPCB 31 is chosen to allow for a small gap of e.g. 200 micrometer. It is only important that there is gap 72 which ensures that the ring electrode portions do not overlap. Within the reflow step, the entire gap will be filled by the liquid catheter tube material. Therefore, the size of the gap 72 should only not be too large to avoid a significant loss of thickness but compared to the entire annular space between the shrink tube and the inner mandrel, the gap volume stays small.

Figure 7B:
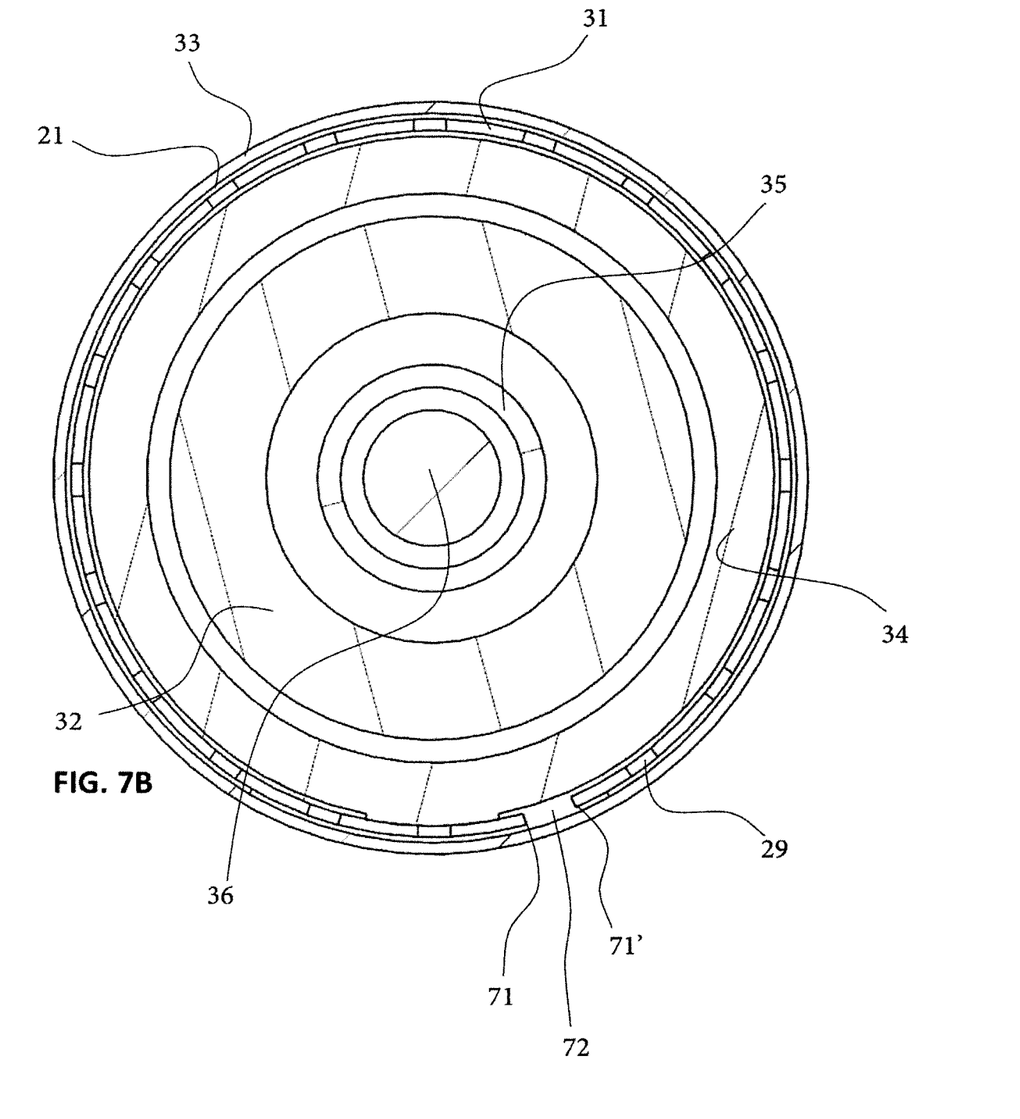
FIG. 7B shows a cross-section view of the lamination assembly of FIG. 3 in the distal electrode segment.

FIG. 7B shows a cross section view of the lamination assembly of FIG. 3 in the proximal electrode segment. The reference numerals and the structure of the cross-section follows the embodiment shown in FIG. 3 in a similar way as FIG. 7A shows the embodiment of FIG. 6. The gap 72 between the edges 71 and 71' is covered by the shrink tube 33. Delamination preventing holes 29 are provided in a distance from the edge 71 of about 200 micrometer. Of course, further holes can be provided around the diameter of the catheter. It is even preferred to have additional holes 29 at various positions around the circumference in different longitudinal positions to enhance the lamination securing effect of the flown catheter material.

The invention claimed is:

1. A method for producing a catheter comprising a flexible printed circuit board (FPCB) having at least one electrode segment at its distal end portion and a FPCB tail leading to a connector at its proximal portion, said method comprising:
   a mandrel inserting step, wherein a temporary mandrel is inserted into a catheter tube,
   a FPCB preshaping step wherein the electrode segment of the FPCB is preshaped in a round hollow cylindrical shape,
   a FPCB positioning step, wherein the preshaped FPCB is positioned on the catheter tube,
   a shrink tube contracting step wherein the assembly including the shrink tube is preheated to the point that the shrink tube has fully contracted and directly contacts and closes the FPCB around the catheter tube,
   a reflow step, wherein the assembly is heated above the melting temperature of the catheter tube to allow the catheter tube material to flow around the FPCB inside the shrink tube,
   a cooling step, wherein the assembly rests until solidification of the assembly material,
   a mandrel removing step, wherein the mandrel is removed from the inner lumen of the re-solidified catheter tube, and
   a shrink tube removal step, wherein the shrink tube is removed.

2. The method according to claim 1, wherein a shrink tube positioning step is provided before the shrink tube contracting step, wherein a shrink tube is positioned around the assembly comprising the FPCB and the catheter tube, and wherein a placement monitoring step is provided after the shrink tube contracting step to check the positioning of the shrink tube, wherein, if the position is estimated non sufficient, the shrink tube positioning step is repeated.

3. The method according to claim 1, wherein a reflow checking step is provided after the reflow step to check if the catheter tube material has fully reflowed the surrounding FPCB and inside the shrinking tube.

4. The method according to claim 1, wherein the shrink tube removal step comprises providing a cut in each side of the shrink tube and peeling it off the laminated unit of FPCB and catheter tube material.

5. The method according to claim 1, wherein the FPCB positioning step further comprises cutting an FPCB tail passage hole in the catheter tube, feeding through the FPCB tail of the FPCB inside the catheter tube.

6. The method according to claim 5, wherein an insertion wire provided at an insertion rod is connected with the connector, and wherein the FPCB tail is fed through displacement of the insertion rod from the distal end of the catheter to the proximal end.

7. The method according to claim 5, wherein before the shrink tube contracting step, a hole covering step is provided, within which the hole is covered by a cut out sheet.

8. The method according to claim 1, wherein, within the FPCB positioning step, the preshaped FPCB is held directly or indirectly via the clamping of the temporary mandrel.

9. The method according to claim 2, wherein, before the shrink tube positioning step, a material adding step is provided, wherein a sheet of reflow material is provided around the FPCB, and wherein the reflow material has a melting temperature similar to the melting temperature of the catheter tube material.

10. The method according to claim 1, wherein, within the FPCB positioning step the preshaped FPCB has a predetermined width being smaller compared to the circumference of the catheter tube so that, when the FPCB is positioned on the catheter tube on the circumference, the electrode edge do not overlap.

11. The method according to claim 1, wherein, within the reflow step, the assembly is heated above the melting temperature of the catheter tube with hot air or thermal radiation directed towards the catheter assembly.

12. The method according to claim 1, wherein, within the reflow step, laser radiation is directed to at least one of the edges of the FPCB and the FPCB tail to weld the LCP material edge of the FPCB material to the catheter tube, wherein the catheter tube is made of TPU or a different laser opaque material.

13. The method according to claim 12, wherein after the reflow step, a smoothing heating step is applied, and wherein the assembly is heated above the melting temperature of the catheter tube with hot air or thermal radiation directed towards the catheter assembly.

14. The method according to claim 1, wherein the FPCB comprises a plurality of delamination preventing holes provided near the edges of the electrodes and/or on a connecting segment of the FPCB tail, and wherein, in the reflow step, the heating is conducted to allow the catheter tube material to flow through the delamination preventing holes.

* * * * *